(12) United States Patent
Tai et al.

(10) Patent No.: US 9,655,774 B2
(45) Date of Patent: May 23, 2017

(54) SMALL MOLECULE TRANSPORT DEVICE FOR DRUG DELIVERY OR WASTE REMOVAL

(71) Applicants: California Institute of Technology, Pasadena, CA (US); University of Southern California, Los Angeles, CA (US)

(72) Inventors: Yu-Chong Tai, Pasadena, CA (US); Nicholas Scianmarello, Pasadena, CA (US); Dongyang Kang, Pasadena, CA (US); Jungwook Park, Pasadena, CA (US); Mark S. Humayun, Glendale, CA (US); Karthik Murali, Los Angeles, CA (US); Amir H. Kashani, Pasadena, CA (US); Hossein Nazari Khanamiri, South Pasadena, CA (US)

(73) Assignees: California Institute of Technology, Pasadena, CA (US); University of Southern California, Los Angeles, CA (US)

(*) Notice: Subject to any disclaimer, the term of this patent is extended or adjusted under 35 U.S.C. 154(b) by 153 days.

(21) Appl. No.: 14/744,439

(22) Filed: Jun. 19, 2015

(65) Prior Publication Data

US 2015/0366707 A1    Dec. 24, 2015

Related U.S. Application Data

(60) Provisional application No. 62/014,617, filed on Jun. 19, 2014, provisional application No. 62/152,495, (Continued)

(51) Int. Cl.
*A61M 5/00* (2006.01)
*A61F 9/00* (2006.01)
(Continued)

(52) U.S. Cl.
CPC ............ *A61F 9/0017* (2013.01); *B29C 39/10* (2013.01); *B29C 65/02* (2013.01);
(Continued)

(58) Field of Classification Search
CPC . B29C 39/10; B29C 66/1142; B29C 66/3242; B29C 66/54; B29C 66/73754;
(Continued)

(56) References Cited

U.S. PATENT DOCUMENTS

| 7,186,232 B1* | 3/2007 | Smedley | A61F 9/00781 |
| | | | 604/294 |
| 8,986,727 B2* | 3/2015 | Martin | A61K 9/0004 |
| | | | 424/425 |
| 2004/0147871 A1 | 7/2004 | Burnett | |

FOREIGN PATENT DOCUMENTS

WO    2014/055989 A1    4/2014

OTHER PUBLICATIONS

Invitation to Pay Additional Fees, Sep. 2, 2015, PCT application No. PCT/US15/3665, 2 pages.
(Continued)

*Primary Examiner* — Philip R Wiest
(74) *Attorney, Agent, or Firm* — Kilpatrick Townsend & Stockton LLP (57) ABSTRACT

A medical device having a permeable bag connected by a non-permeable cannula to a discharge sac is described along with a manufacturing process and surgical implantation method. The permeable portions of the device have pores that are sized to be permeable to a predetermined class of small molecules, such as oxygen, nitrous oxide, or other therapeutic agents. Once absorbed inside the device, the small molecules are then passively transported, by a concentration gradient of the small molecules, to the discharge sac to be disbursed. A metal tube or other strip can be
(Continued)

included in the cannula to assist a surgeon in orienting the device within the body.

20 Claims, 9 Drawing Sheets

Related U.S. Application Data filed on Apr. 24, 2015, provisional application No. 62/104,568, filed on Jan. 16, 2015.

(51) Int. Cl.
| | |
|---|---|
| *B29C 39/10* | (2006.01) |
| *B29C 65/00* | (2006.01) |
| *B29C 65/02* | (2006.01) |
| *B29K 83/00* | (2006.01) |
| *B29C 41/36* | (2006.01) |
| *B29L 31/00* | (2006.01) |

(52) U.S. Cl.
CPC ...... *B29C 66/1142* (2013.01); *B29C 66/3242* (2013.01); *B29C 66/54* (2013.01); *B29C 66/73754* (2013.01); *A61F 2240/001* (2013.01); *B29C 41/36* (2013.01); *B29C 66/71* (2013.01); *B29C 66/919* (2013.01); *B29C 66/949* (2013.01); *B29K 2083/005* (2013.01); *B29L 2031/7548* (2013.01)

(58) Field of Classification Search
CPC ..... B29C 41/36; B29C 66/71; A61F 9/00781; A61F 9/0017
USPC .................................................. 604/8–10
See application file for complete search history.

(56) References Cited

OTHER PUBLICATIONS

Abdallah et al., "Vitreal Oxygenation in Retinal Ischemia Reperfusion," Invest Ophthalmol. Vis. Sci., Feb. 2011, vol. 52(2), pp. 1035-1042.

Balachandran et al., "Contribution of Saccadic Motion to Intravitreal Drug Transport," Pharm Res, 2011, vol. 28, pp. 1049-1064.

Barbazetto et al., "Oxygen tension in the rabbit lens and vitreous before and after vitrectomy," Experimental Eye Research, 2004, vol. 78, pp. 917-924.

Clarkson et al., "Natural History and Clinical Management of Central Retinal Vein Occlusion," Arch Ophthalmol., 1997, vol. 115, pp. 486-491.

Congdon et al., "Causes and Prevalence of Visual Impairment Among Adults in the United States," Arch Ophthalmol., 2004, vol. 122, pp. 477-485.

Eison-Perchonok et al., "Kinetics of Ascorbic Acid Autoxidation as a Function of Dissolved Oxygen Concentration and Temperature," Journal of Food Science, 1982, vol. 47, pp. 765-767, 773.

Filas et al., "Computational Model for Oxygen Transport and Consumption in Human Vitreous," Invest. Ophthalmol Vis Sci., 2013, vol. 54, pp. 6549-6559.

Goto et al., "Frequency and Risk Factors for Neovascular Glaucoma After Vitrectomy in Eyes with Proliferative Diabetic Retinopathy," J. Glaucoma, 2013, vol. 22, pp. 572-576.

Hayreh, "Management of Central Retinal Vein Occlusion," Ophthalmologica, May/Jun. 2003, vol. 217, pp. 167-188.

Kampen et al., "The Prevalence of Diabetic Retinopathy Among Adults in the United States," Arch Ophthalmol., 2004, vol. 122, pp. 552-563.

Kim et al., "Mathematical Analysis of Oxygen Transfer Through Polydimethylsiloxane Membrane Between Double Layers of Cell Culture Channel and Gas Chamber in Microfluidic Oxygenator," Microfluidics and Nanofluidics, 2013, vol. 15, pp. 285-296.

Klein et al., "The 15-Year Cumulative Incidence of Retinal Vein Occlusion," Arch Ophthalmol., 2008, vol. 126(4), pp. 513-518.

Landers et al., "Panretinal Photocoagulation and Retinal Oxygenation," Retina, 1982, vol. 2, pp. 167-175.

McIntosh et al., "Natural History of Central Retinal Vein Occlusion: An Evidence-Based Systematic Review," Ophthalmology, 2010, vol. 117, pp. 1113-1123.

Roos, "Theoretical estimation of retinal oxygenation during retinal artery occlusion," Physiol. Meas., 2004, vol. 25, pp. 1523-1532.

Roy et al., "The Prevalence of Diabetic Retinopathy Among Adult Type 1 Diabetic Persons in the United States," Arch Ophthalmol., 2004, vol. 122, pp. 546-551.

Shui et al., "The Gel State of the Vitreous and Ascorbate-Dependent Oxygen Consumption," Arch Ophthalmol., 2009, vol. 127(4), pp. 475-482.

Stocchino et al., "Eye rotation induced dynamics of a Newtonian fluid within the vitreous cavity: the effect of the chamber shape," Phys. Med. Biol., 2007, vol. 52, pp. 2021-2034.

\* cited by examiner

SMALL MOLECULE TRANSPORT DEVICE FOR DRUG DELIVERY OR WASTE REMOVAL

CROSS-REFERENCES TO RELATED APPLICATIONS

This application claims the benefit of U.S. Provisional Application No. 62/152,495, filed Apr. 24, 2015, U.S. Provisional Application No. 62/104,568, filed Jan. 16, 2015, and U.S. Provisional Application No. 62/014,617, filed Jun. 19, 2014, which are hereby incorporated by reference in their entireties for all purposes.

STATEMENT AS TO RIGHTS TO INVENTIONS MADE UNDER FEDERALLY SPONSORED RESEARCH AND DEVELOPMENT

This invention was made with government support under EY022059 awarded by the National Institutes of Health. The government has certain rights in the invention.

BACKGROUND

1. Field of the Art

Generally, embodiments of the present invention relate to methods and devices for treatment of the eyes and other areas within the body. More specifically, embodiments relate to implantable devices for capturing small molecule therapeutic agents or waste material and transporting them to and from structures within the body.

2. Description of the Related Art

In the United States, the leading cause of blindness is diabetic retinopathy. Diabetic retinopathy is caused by retinal ischemia, that is, inadequate blood flow to the retina caused by capillary nonperfusion. The lack of capillary blood flow starves the retina of oxygen. Retinal vein occlusion also occurs in which small veins that move blood away from the retina are blocked. A subject with retinopathy loses vision over time as retinal cells in his or her eyes die.

Other areas of the body besides the eyes can experience lack of blood flow caused by diabetes or other ailments. Restriction of blood flow to a particular portion of the body is simply called ischemia. Ischemia is often accompanied by hypoxia, which refers to the lack of oxygen ($O_2$) that blood delivers. Ischemic insults often cause severe tissue hypoxia and ultimately tissue death.

Current treatment methods for ischemic diseases are limited and do not necessarily treat the primary cause of the disease—that is, hypoxia. The mainstay of treatment for capillary nonperfusion or areas of ischemia is laser ablation. This treatment is destructive, irreversible, and can cause additional organ loss. Systemic administration of oxygen is also an option, but toting around pure oxygen or scheduling appointments for oxygen injections carries risks and is inconvenient for subjects.

Retinal ischemia can be treated with the above methods, but such treatments in the eye carry additional drawbacks. For example, laser ablation and photocoagulation can result in a constricted peripheral visual field as well as delayed dark adaptation. Other treatments have been developed for the eye, such as intravitreal injections and pars plana vitrectomies. Intravitreal injections often need to be repeated frequently and poses significant risk and cost to the patient and healthcare system. Intravitreal injections use therapeutic agents that only suppress downstream effects of the hypoxia on retinal tissue. A pars plana vitrectomy, which removes a portion of vitreous humor from the eye, may result in insufficient amounts of retinal oxygen while causing cataracts or other potential oxygen toxicity near the lens. Indeed, too much oxygen near the front (anterior) inside of the eyeball near the lens is a bad thing. It can also increase the risk of iris neovascularization as well as elevated intraocular pressure.

Therefore the current armamentarium of treatments for ischemic retinal and other diseases has a number of distinct disadvantages that need to be overcome.

BRIEF SUMMARY

Generally described is a microfabricated, implantable medical device with two permeable-bag ends connected by a nonpermeable tube in the middle. The bags are fabricated to be permeable to a specific class of small molecules of interest, such as diatomic oxygen ($O_2$) or other "drugs." The bags can be sized to collect and disburse a calculated amount of the small molecules and transfer them by passive means, that is, by virtue of there being a higher concentration of the molecules in one region than another region. Proteins to assist in the capture and transport of the target small molecule can also be included within the device.

The tube between the permeable bags can include a strip of pliable, bendable material, such as metal, so that a surgeon can bend the tube and keep it bent in order to align the device in the body. For example, the device can be mounted so that its tube enters the pars plana of an eyeball and bends back so that its discharge bag is near the retina. Suture holes and handles can be included to assist implantation.

Also described are methods of microfabrication of the device from biocompatible silicone and parylene C. Microfabrication can include using custom molds based on measurements of a subject's oxygen deficiency, among other things. Not only can the size of the bags can be customized depending on a particular patient's oxygen deficiency, but the thickness of the bags can also be customized Methods for implantation for the device are also described.

Some embodiments of the present invention are related to a biocompatible, implantable apparatus for collecting and redistributing a predetermined class of small molecules within a body. The apparatus includes a permeable absorption bag, the bag being permeable to a predetermined class of small molecules, the bag defining an interior, a flexible cannula having a lumen, the cannula having a portion that is nonpermeable to the small molecules, and a foldable or rollable discharge sac, the sac being permeable to the small molecules, the sac defining an interior, wherein the lumen of the cannula connects the interior of the absorption bag to the interior of the discharge sac.

The apparatus can include a pliable strip attached to the cannula and adapted to maintain the cannula in a bent or straight shape. The pliable strip can be enclosed within the cannula, include a foil, sheet, rod, or tube, and/or be comprised of a metal. At least a portion of the absorption bag, cannula, and discharge sac can be integrally formed of silicone. Parylene can coat the silicone of the cannula, thereby reducing a permeability of the cannula. The absorption bag, cannula, and discharge sac can be produced by micro-fabrication and thus have squared edges and be approximately the same height. A tab can extend from the absorption bag, the flap having a suture hole therethrough. A handle can extend from the absorption bag, the handle being suitable for tugging with a surgical tool. The discharge sac is toroidal shaped, an inner radius of the toroidal shaped discharge sac being equal to or greater than 6 millimeters.

At least one pillar can be disposed within the cannula, the at least one pillar adapted to keep the cannula lumen from pinching closed. The at least one pillar can have a cross section selected from the group consisting of an I-shaped cross section, an O-shaped cross section, and an X-shaped cross section. The cannula can have a perimeter less than or equal to 6 millimeters, thereby enabled to be fit through a 3-millimeter or larger incision in a pars plana.

The predetermined class of small molecules can include diatomic oxygen ($O_2$). A perfluorocarbon can be included within the absorption bag for oxygen solubility. A hemeprotein can be included within the absorption bag for oxygen transport. The hemeprotein can include a natural, artificial, or autologous hemoglobin or myoglobin. A chlorocruorin or hemocyanin can be included within the absorption bag for oxygen transport. The predetermined class of small molecules can include carbon dioxide ($CO_2$) or nitrous oxide ($N_2O$). The predetermined class of small molecules can include a therapeutic agent or a waste product.

An oxygen sensor can be placed proximate to the discharge sac, and an antenna can be attached to the oxygen sensor. The oxygen sensor can be configured to be powered from radio frequency (RF) energy through the antenna.

The absorption bag and discharge sac can have pores dimensioned to be between about 1 to about 5 times a Stokes diameter of the small molecules. The absorption bag can be about 10 millimeters (mm) in diameter, the cannula can have a perimeter of about 4 mm, and the discharge sac can be about 4.5 mm in diameter.

The apparatus can be attached to an eyeball of a human or nonhuman organism, the absorption bag placed between a conjunctiva and sclera of the eyeball, the cannula penetrating the sclera through a pars plana of the eyeball, and the discharge sac within posterior vitreous of the eyeball.

Some embodiments are related to a method of manufacturing an implantable small molecule collection and redistribution apparatus. The method can include spreading uncured, biocompatible silicone on dumbbell-shaped half molds, partially curing the silicone on the half molds to create partially cured silicone halves, peeling one of the partially cured halves from one of the half-molds, applying uncured silicon to one of the partially cured silicone halves, aligning and joining the partially cured halves, further curing the partially cured halves to create an integrally formed silicone workpiece comprising a bag connected by a cannula to a sac, masking at least a portion of the bag and at least a portion of the sac, and depositing parylene on the cannula, thereby reducing a permeability of the cannula and forming a small molecule collection and redistribution apparatus.

The method can include placing a strip of pliable metal along the uncured silicone of a handle portion of the dumbbell-shaped half molds. The method can include measuring a partial pressure of a predetermined class of small molecules within a subject, and creating a photolithography mask that is sized based on the measured partial pressure within the subject. The method can include exposing a photoresist on a substrate to masked electromagnetic radiation, and developing the photoresist to create the half molds. The parylene can be deposited using chemical vapor deposition (CVD).

Some embodiments are related to a method of surgically implanting an oxygen collection and redistribution apparatus in an eyeball of a subject. The method can include providing an oxygen collection and redistribution apparatus having a permeable absorption bag, a flexible cannula, a pliable metal strip within the cannula, and a foldable or rollable discharge sac, wherein a lumen of the cannula connects an interior of the absorption bag to an interior of the discharge sac, cutting an incision through an eyeball of a subject, the incision being less than 3 millimeters long, bending the cannula with the pliable metal strip, pulling the discharge sac and a portion of the cannula through the incision, placing the absorption bag between a conjunctiva and sclera of the eyeball, suturing the absorption bag to the sclera, and orienting the cannula such that the discharge sac is within a posterior vitreous of the eyeball.

The discharge sac can be toroidal shaped, and the method can include centering an internal diameter of the toroidal shaped discharge sac with an optical axis of the eyeball in order to keep a light path clear.

A further understanding of the nature and the advantages of the embodiments disclosed and suggested herein may be realized by reference to the remaining portions of the specification and the attached drawings.

DETAILED DESCRIPTION

Medical devices, their methods of manufacture, and surgical methods for their implantation are described. The medical devices capture, in the body, any biologically or chemically active agent that may have therapeutic benefits. They then deliver the agent to another part of the body. The device can also be used for removing waste or any non-therapeutic material from one area of the body to another.

Particularly described as an exemplary device to treat ischemic retinal diseases by passively supplying oxygen. The device transports oxygen from an oxygen-rich zone into an oxygen deficient one based on a natural concentration gradient. In an example case of retinal ischemia, this can be from the subconjunctival space into the vitreous cavity. This may prevent a further decline of vision, avoid laser photocoagulation, and possibly avoid a pars plana vitrectomy.

International Publication No. WO 2014/055989 A1, which is owned by applicants, describes an active oxygenator prototype. The active oxygenator prototype generates oxygen from electrolysis of water within an enclosed device. The oxygen then selectively diffuses through a predesignated part of a cannula. The device is replenished by needle injection when its reservoir is depleted.

In contrast, an embodiment of the present invention can treat ischemia through passive oxygen delivery to an ischemic or deficient region.

Figure 1:
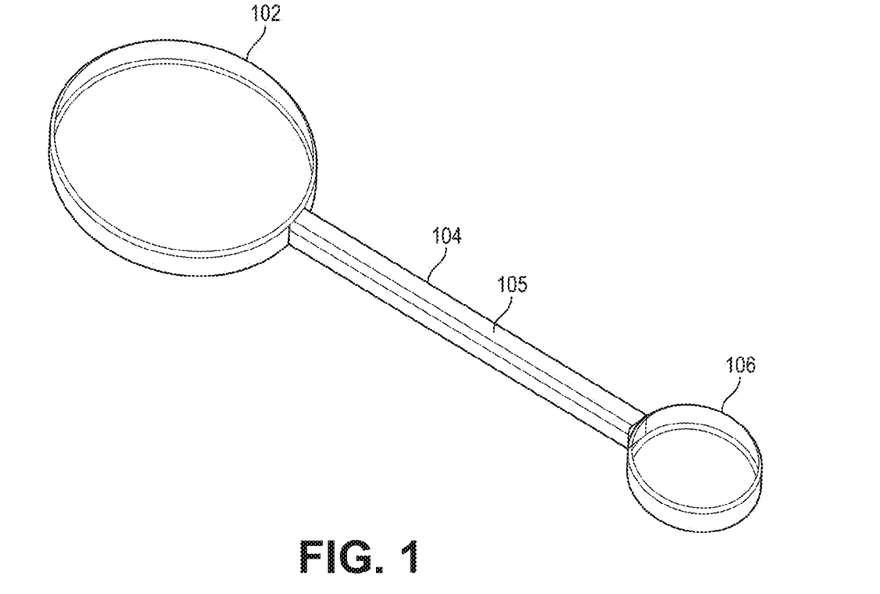
FIG. 1 illustrates a device in accordance with an embodiment.

FIG. 1 illustrates a device in accordance with an embodiment. Device 100 is comprised of permeable absorption bag 102, non-permeable cannula 104, and permeable discharge sac 106. Absorption bag 102 absorbs oxygen from an oxygen rich zone. Cannula 104 is a thin tube to transport the oxygen. Discharge sac 106 releases or diffuses the oxygen to a targeted region.

Absorption bag 102, cannula 104, and discharge sac 106 are made of biocompatible silicone that has been cured together, i.e., integrally formed. Parylene C coating 105 surrounds cannula 104, lowering the cannula's permeability to the point of non-permeability. Parylene C is a biocompatible polymer with a permeability rate that is five orders of magnitude lower than silicone.

"Permeability" of a material is typically in relation to a size of substance of interest. A Stokes-Einstein radius or a Stokes diameter is a measure of the diffusion properties of a substance. A "Stokes diameter" is an equivalent diameter of a hard sphere that a molecule possesses in terms of its diffusion rate. A molecule can pass through thin materials with pores that have a Stokes diameter that is about 1 to about 5 times the Stokes diameter of the molecule.

"About" includes within a tolerance of ±0.01%, ±0.1%, ±1%, ±2%, ±3%, ±4%, ±5%, ±8%, ±10%, ±15%, ±20%, ±25%, or as otherwise known in the art.

Drug (e.g., oxygen) diffusion out of discharge sac 106 into a deficient region of the body lowers the device's internal concentration, an this in turn pulls oxygen from an oxygen rich region into the device. The concentration gradient will continue to transport oxygen from the outside of the eye to the inside of the vitreous cavity.

Bubble formation on the surface of the device can be prevented by performing hydrophobic and hydrophilic surface modifications. This can prevent gas accumulation on the surface and allow for only the dissolved drug to be delivered.

Dosing and targeted release can be controlled by material properties of the device. Controlling the thickness of silicone can determine the permeation rate (dosing). As absorption bag 102, cannula 104, and discharge sac 106 are integrally formed with the same thickness of silicone, a single adjustment to how much silicone is distributed on a mold can determine the bag's and sac's permeation rates. Cannula 104 is coated with a non-permeable coating, and thus its permeability is ideally relatively independent of how much silicone is distributed on the molds.

The diameter of the absorption bag and diameter of the discharge sac can also be adjusted to alter the permeation rate. The shape of the device and surface areas of the absorption bag and discharge sac are application dependent and can be designed for the specific task the device is to perform.

In addition to controlling the thickness, one may inject into the interior of the device a substance with a high diffusion constant, or high oxygen solubility, such as perfluorocarbons, air, etc. For example, a perfluorocarbon within the absorption bag and device can increase oxygen solubility. A hemeprotein, such as a natural, artificial, or autologous hemoglobin or myoglobin, can be added inside the device to increase oxygen transport. A chlorocruorin or a hemocyanin can be added into the absorption bag and other portions of the device to increase oxygen transport. Other substances natural or synthetic that have beneficial properties for oxygen storage or transport may be used.

Other small molecules besides diatomic oxygen can also be captured and transported. The device can be targeted for carbon dioxide ($CO_2$), nitrous oxide ($N_2O$), or other gases. Small molecule proteins and other drugs can be specifically targeted. Any of these 'drugs' may be transported, whether they are classified as a therapeutic agent, waste product, or otherwise.

The exemplary device does not require any electronics or reservoir, allowing it to be thin. For applications in the eye, a thinner device reduces abrasion and wearing down of the conjunctiva that would cover the device. However, if necessary, electronic monitoring of oxygen concentration, pH values, etc., may be added.

Figure 2:
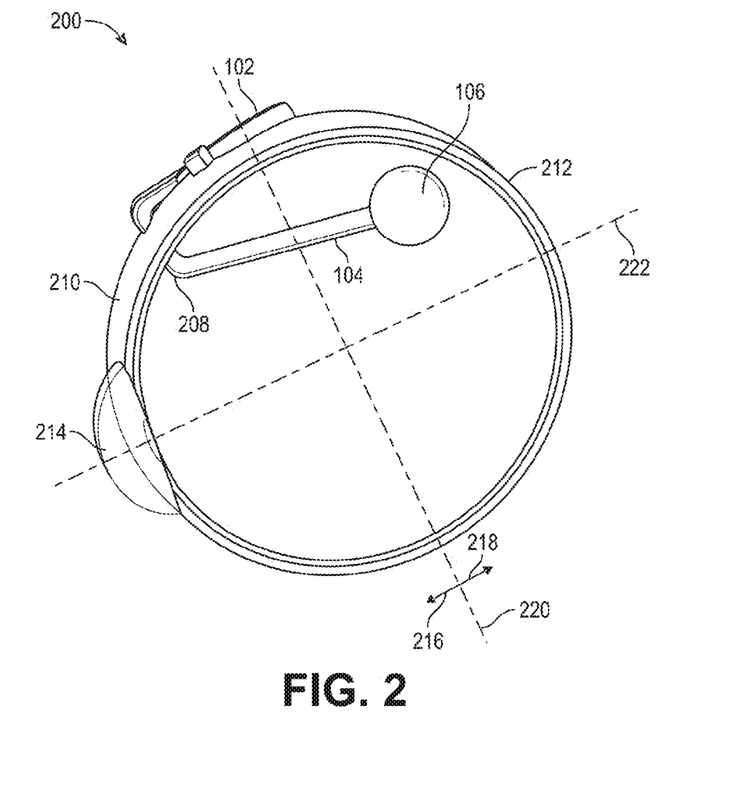
FIG. 2 illustrates a device implanted within an eyeball in accordance with an embodiment.

FIG. 2 illustrates a device implanted within an eyeball in accordance with an embodiment. In installation 200, absorption bag 102 is implanted outside of sclera 210 and underneath the conjunctiva (not shown in the figure). Precisely, it is located in the supraconjunctival area, extending from 2 mm behind the limbus to the equator. After penetrating they eyeball at the pars plana, flexible cannula 104 incurs bend 208 to project it back toward macula 212 and away from lens 214. That is, cannula 104 extends from anterior region 216 of the eye past midplane 220 to posterior region 218. Cannula 104 terminates at discharge sac 106, which is placed just outside of optical axis 222 of the eyeball in order to keep the eye's light path clear.

Cannula 104 is preferably small in order to minimize the size of the incision during surgery. For example, the cannula can be made have a perimeter or circumference less than 6 mm in order to fit within a 3 mm or larger incision. Since the discharge sac is made of thin silicone and is foldable and/or rollable, its flexibility would allow it enter through a small incision.

In the case of retinal ischemia, the conjunctiva has fairly high oxygen permeation. Data shows about that the partial pressure of oxygen is 100 millimeters of mercury (mmHg) under a rabbit conjunctiva when the eye is open and the sclera is visible. The sclera, however, has relatively low oxygen permeation into the vitreous humor. The ischemic eye has an oxygen concentration of 15 mmHg.

Transporting oxygen from underneath the conjunctiva into the vitreous, using passive means alone, has been shown to be feasible. The absorption bag is placed in the subconjuctival region, resting on the sclera. The cannula penetrates the sclera at the pars plana and travels towards the peripheral vitreous. There, the discharge sac, sometimes called a diffuser, is located to provide oxygen for the retina. So long as the eye is open, oxygen in the subconjuctival area should be sufficient for the ischemic eye.

The gel nature of the vitreous impedes rapid convection of oxygen through the interior of the eye. This, while generally a detriment, can be used to the device's benefit. A partial vitrectomy can allow the region near the retina to be replaced with saline, allowing for the fast convective transport of oxygen to reach high oxygen concentration near the retina where it is desired, while leaving the anterior of the eye to have only diffusive transport. This keeps the oxygen partial pressure low near the lens, which reduces the risk of cataracts and other potential oxygen toxicity.

Embodiments are not limited to the eye. Delivering oxygen from areas of high oxygen tension to areas with low oxygen tension can be used to treat any disease process which causes hypoxia or to alleviate any hypoxic conditions, preferably before irreversible damage is done. For example, one embodiment may include a subdermal implant which oxygenates blood in patients who are hypoxic. Another embodiment may include an implant to deliver oxygen to parts of the central nervous system to alleviate hypoxia from an ischemic stroke.

Ischemia can be found throughout the body in many disease processes, and with differing form factors embodiment devices can help treat it. For example, an embodiment can be used to deliver or manipulate the distribution of other gases in the body. Carbon dioxide and nitrous oxide are biologically active gases that have important physiological roles. They may be redistributed in order to normalize a pathological process. For example, patients with chronic obstructive pulmonary disease may retain carbon dioxide in pathologic amounts. An embodiment can be used to shunt excess levels of carbon dioxide and avoid toxic buildup of this gas. Exemplary embodiments show implantation in and around an eye; however, the placement in other areas of the body as described above, and their suitable configurations, are contemplated. The configurations may include other parts to aid in compatibility with the other areas of the body as well as in surgery to implant the device.

To allow the device to be bent during surgery into the exact location chosen by the surgeon, the cannula may contain a metal sheet or plate that can easily be manipulated so as to rigidly maintain the device's shape and location.

Figure 3:
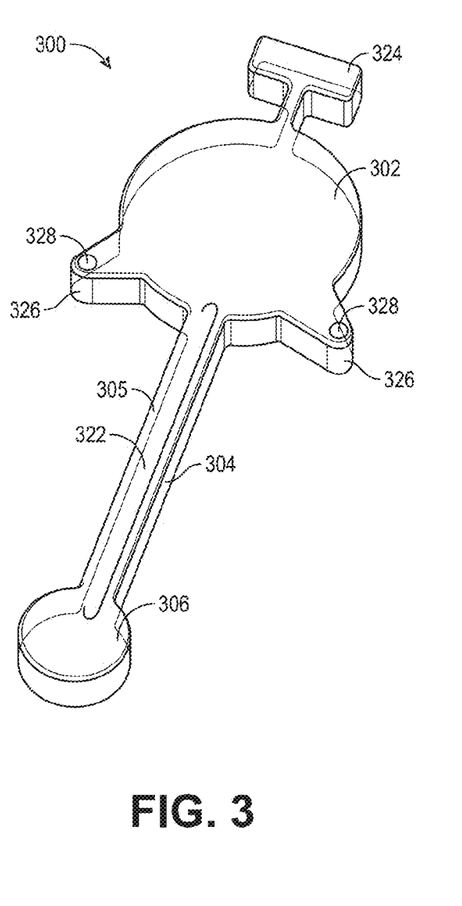
FIG. 3 illustrates a device with suture holes in accordance with an embodiment.

FIG. 3 illustrates a device with suture holes in accordance with an embodiment. Device 300 includes absorption bag 302, cannula 304, and diffusion sac 306. Cannula 304 is covered in a thin parylene coating 305.

Enclosed inside cannula 304 is pliable metal strip 322, which is a biocompatible type 304 stainless steel tube. The tube is pliable so that it can be bent and keep its bent shape. Or it can be re-bent to be straight and then keep its straight shape. In other embodiments, the metal strip may be a thin metal foil, sheet, or solid rod. Strip 322 can be bent by a surgeon's hands or by surgical instruments.

Device 300 includes tabs 326 spaced symmetrically across from each other, each tab 326 having through hole 328. Through holes 328 are sized for sutures and thus are sometimes called suture holes.

Handle 324 attached to bag 302 is T-shaped, allowing for tweezers or other surgical tools to gain purchase of the absorption bag material without tearing it. A surgeon can pull the discharge sac and cannula through an incision which holding the absorption bag by handle 324. Further, handle 324 can be used to hold absorption bag 302 in place while suturing it in place.

Figure 4:
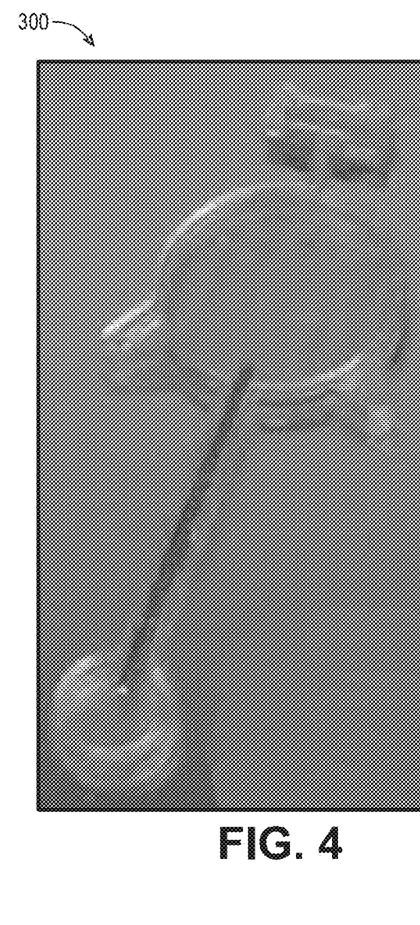
FIG. 4 is a photograph of a device corresponding to that of FIG. 3.

FIG. 4 is a photograph of a device corresponding to the line drawing of FIG. 3. Device 300 is composed of clear silicone, allowing the metal tube through the cannula to show through.

Figure 5:
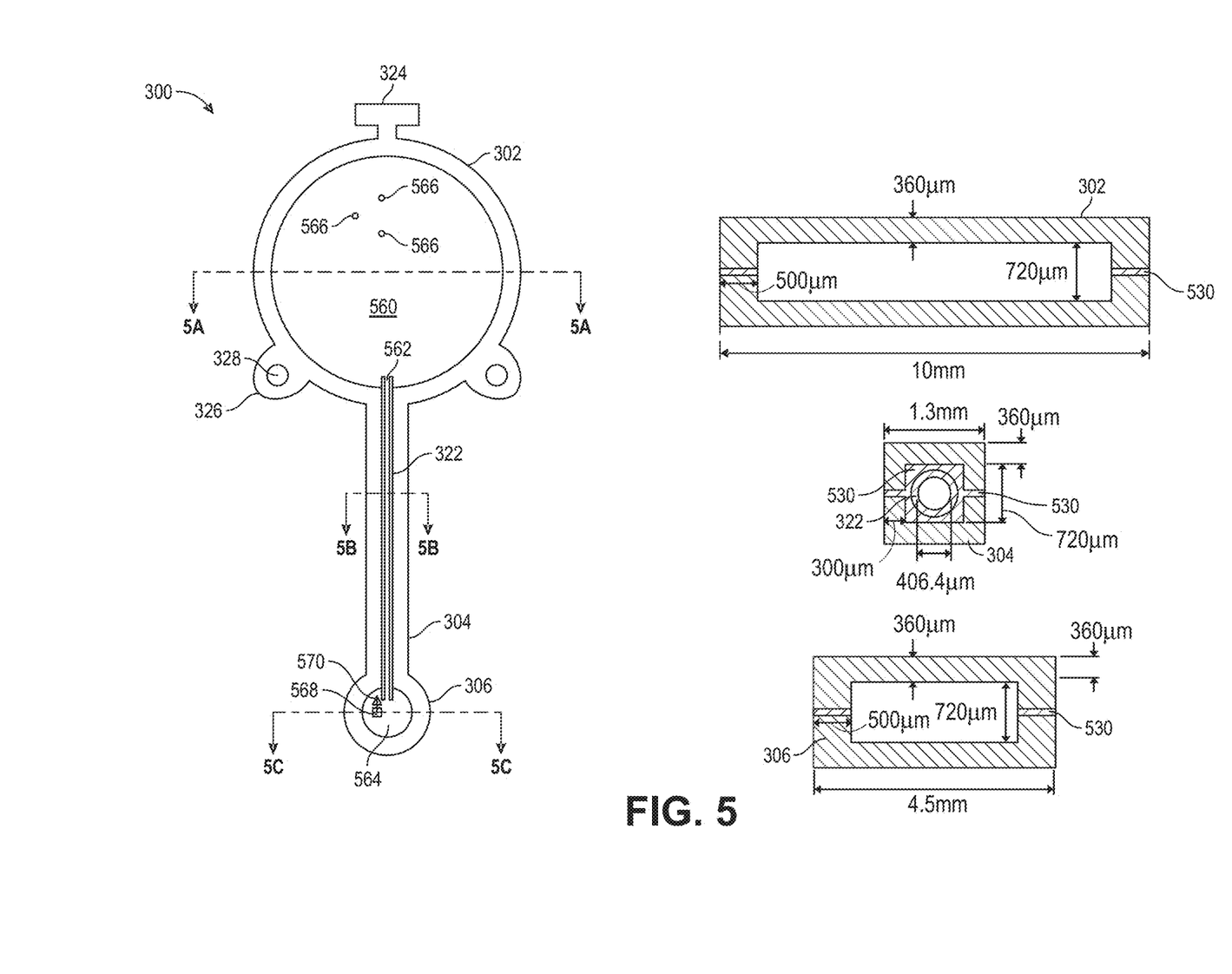
FIG. 5 illustrates a plan view and cross sectional views of the device of FIG. 3.

FIG. 5 illustrates a plan view and cross sectional views of the device of FIG. 3. In the exemplary embodiment, absorption bag 302 is 10 mm in diameter with 500 μm (micron) walls. The internal height is 720 μm with a ceiling and a floor thickness of 360 μm each, for a total thickness of 1440 μm. Cannula 304 is 12 mm long with a width of 1.3 mm. Like the absorption bag, the cannula has an internal height of 720 μm with a ceiling and a floor thickness of 360 μm each, for a total thickness of 1440 μm. The side walls are 300 μm thick.

Tube 322 has an internal diameter of 406.4 μm (0.016 inches) and an outside diameter of 508 μm (0.02 inches). Discharge sac 306 is 4.5 mm in diameter with 500 μm (micron) walls. The internal height is 720 μm with a ceiling and a floor thickness of 360 μm each, for a total thickness of 1440 μm, just like that of the absorption bag and cannula. That the absorption bag 302, cannula 304, and discharge sac 306 have squared edges and are all approximately the same height is an indication that they were fabricated together using lithographic techniques.

Inside absorption bag 302 of device 300 can be perfluorocarbons 566 to increase the absorption of oxygen by the absorption bag. Permeable material 560, which forms the envelope of absorption bag 302, is silicone. A particular silicone that has been shown to be effective is NuSil Technology LLC (of Carpinteria, Calif., U.S.A.) MED4-4210, two-part, medical grade silicone in which base and curing agent are mixed at a 10:1 ratio by weight. Permeable material 564, which forms the envelope of discharge sac 306 is formed of the same silicone.

Handle 324 and tabs 326 with holes 328 are integrally formed with device 300. That is, the silicone of these appurtenances are at least partially co-cured with that of absorption bag 302, cannula 304, and discharge sac 306. As will be detailed below, a thin layer of uncured silicone 530 is spread between partially-cured halves of the device before fully curing the device's silicone material. Further, uncured silicone 530 is spread in cannula 304 before metal tube 322 is placed therein. Tube 322 keeps lumen 562 free from flowing silicone while curing.

Oxygen sensor 568 is located inside discharge sac. It is powered by radio frequency (RF) energy from a physician's external device, through antenna 570. When a physician energizes his or her reader, RF energy wakes up the oxygen sensor for one or more readings of the oxygen levels in the discharge sac. Antenna 570 transmits the readings to the external device, where they can be assessed.

Figure 6:
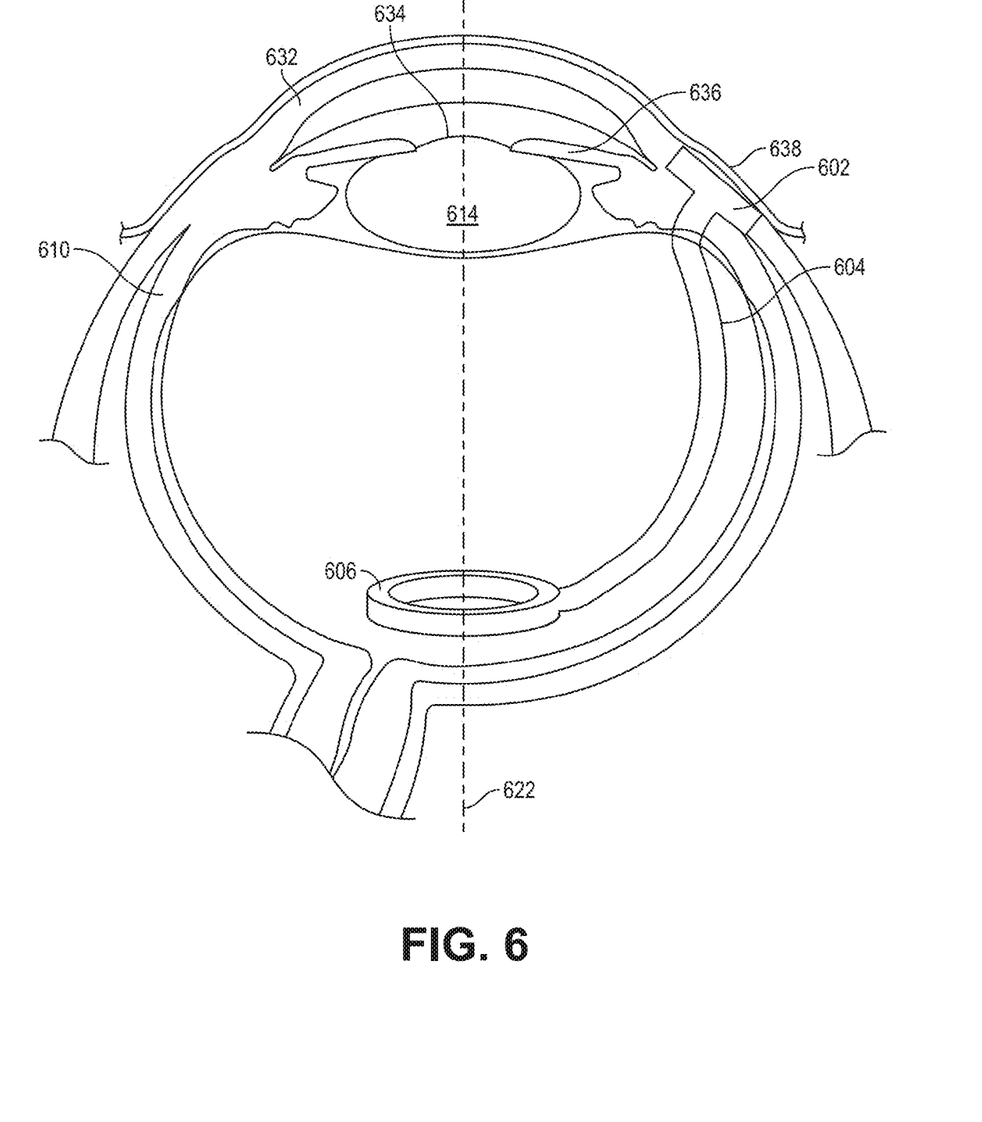
FIG. 6 illustrates bag placement in a subconjunctival space in accordance with an embodiment.

FIG. 6 illustrates bag placement in a subconjunctival space of an eyeball in accordance with an embodiment. To the side of lens 614, cornea 632, pupil 634, and iris 636, absorption bag 602 sits under conjunctiva 638. Cannula 604 pierces sclera 610, turns to the rear, and ends up near the retina. Discharge bag 606 connects with cannula 604 such that the interior of absorption bag 602 is connected in a constant fluid path to the interior of discharge sac 606.

Discharge sac 606 is toroidal (i.e., ring) shaped. An inside diameter of discharge sac 606 is positioned such that it is symmetrically placed around optical axis 622. Thus, discharge sac surrounds and circumscribes the retina.

Figure 7A:
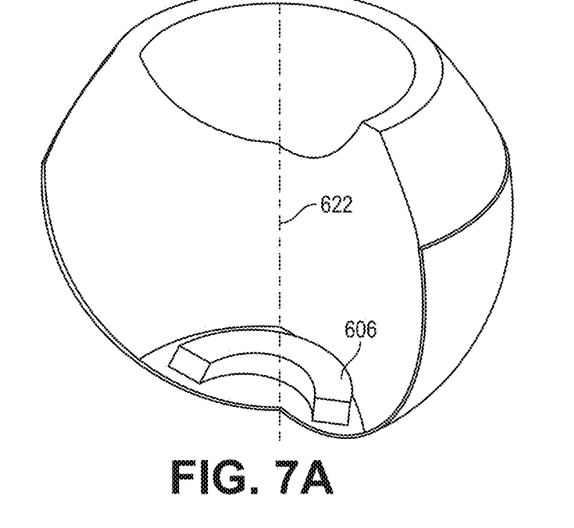
FIG. 7A is a cut-away perspective view of a toroidal sac placement in accordance with an embodiment.
Figure 7B:
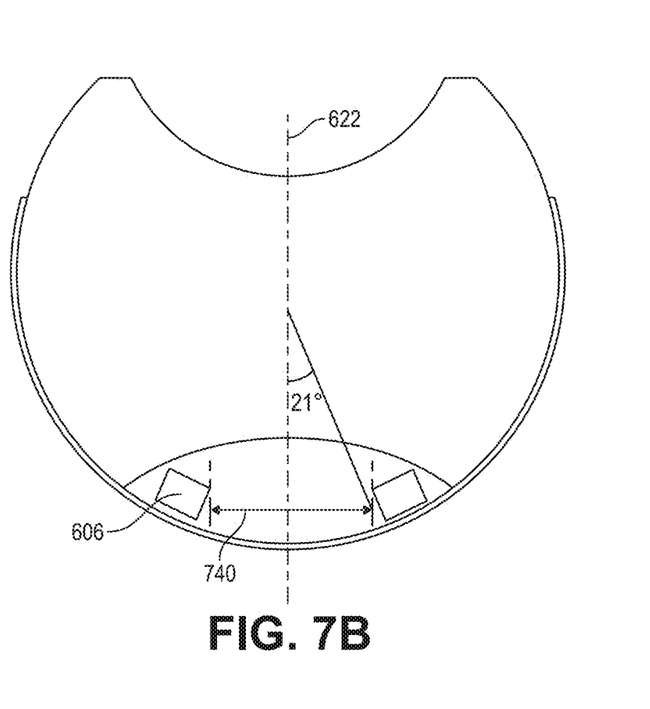
FIG. 7B is a cross section view of a toroidal sac placement in accordance with an embodiment.

FIGS. 7A and 7B are cut-away views of a toroidal sac placement in accordance with an embodiment. A cut-away of discharge sac 606 shows it with a rectangular cross section with squared edges. This is a product of it having been manufactured using lithographic fabrication means.

Internal diameter 740 of the toroidal shaped discharge sac 606 is 6 millimeters. This keeps it close enough to the retina to effectively distribute oxygen for therapeutic effects while keeping it far enough away from the optical volume so that it does not interfere with the eye's imaging capability.

Figure 8:
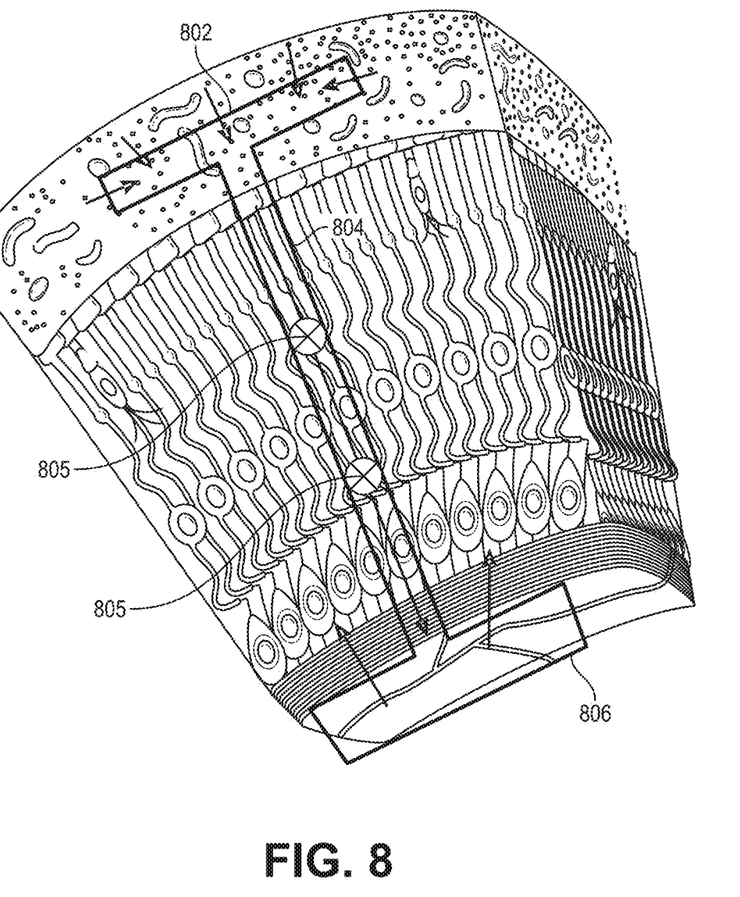
FIG. 8 illustrates bag placement in a choroid space in accordance with an embodiment.

FIG. 8 illustrates bag placement in a choroid space in accordance with an embodiment. In this configuration, absorption bag 802 is placed within the choroid, just outside the pigmented layer of the eye.

Cannula 804 penetrates through the rod and cone photoreceptor cells, horizontal cells, bipolar cells, amacrine cells, ganglion cells, and the axons of the ganglion cells to the optic nerve. X-shaped pillars 805 are disposed within cannula 804. They are present in order to keep a lumen of cannula 804 from pinching closed. Alternatively or in addition, O-shaped and I-shaped pillars can be formed within cannula in order to keep it open.

FIGS. 9A-9F illustrate a manufacturing process for an exemplary embodiment in accordance with an embodiment.

Figure 9A:
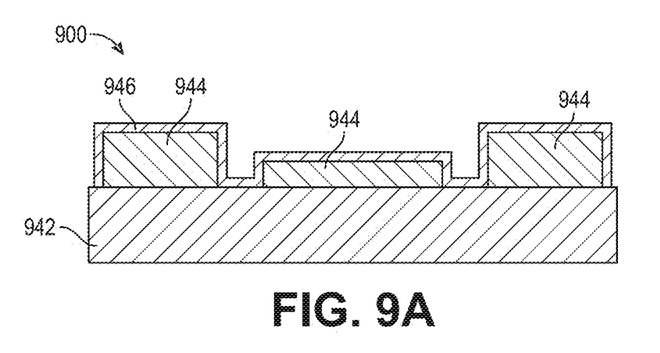
FIG. 9A illustrates a prepared top half mold in accordance with an embodiment.

In FIG. 9A, top half mold 900 includes silicon substrate 942 with dry film photoresist 944 patterned in the "dumbbell shape" of the final product.

The photoresist was masked and exposed to visible or ultraviolet (UV) light or other electromagnetic radiation and then developed to create the half molds. Because such masks can be easily altered, a patient's device can be custom made using custom molds. One can first measure the partial pressure of oxygen or other class of small molecules in the conjunctiva and posterior of a subject's eye and then create a photolithography mask that is sized based on the measured partial pressure. For example, a larger dispersion sac may be needed when a subject has a larger area of his or her retina that is oxygen deprived.

The top half of the mold has both the cavity and the top of the device, while the second, bottom half mold has the remaining section. The top mold is coated entirely with coating 946 of parylene C in order to reduce adhesion between silicone and the mold and thus increase the mold's releasability.

Figure 9B:
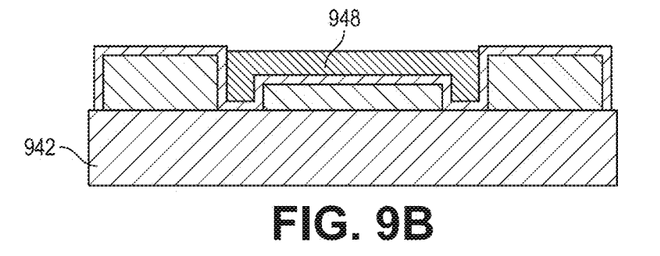
FIG. 9B illustrates spreading silicone over a top half mold in accordance with an embodiment.

In FIG. 9B, uncured silicone 948 is dabbed and brushed upon the top mold so as to coat the bottom and sides. It is then partially cured at 65° C. for 30 minutes.

Figure 9C:
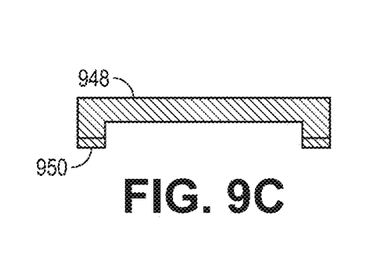
FIG. 9C illustrates a peeled partially cured top half in accordance with an embodiment.

In FIG. 9C, partially cured silicone 948 is peeled from the top mold. Its joining edges are then coated with uncured silicone 950. A pliable tube of malleable, ductile metal is cut to a desired length and inserted in the cannula, "handle section" of the dumbbell shaped apparatus.

Figure 9D:
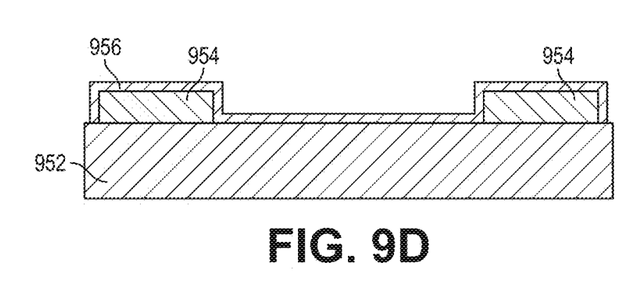
FIG. 9D illustrates a prepared bottom half mold in accordance with an embodiment.

In FIG. 9D, a bottom half mold includes silicon substrate 952 with dry film photoresist 954 patterned in a complementary shape to the top mold. The photoresist is masked, exposed, and developed similarly to that of the photoresist for the top mold. The bottom half mold is coated with parylene C, similarly to that of the top mold.

Figure 9E:
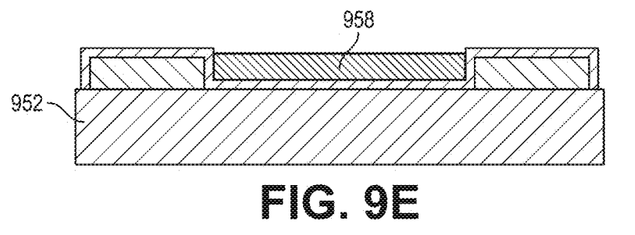
FIG. 9E illustrates spreading silicone over a bottom half mold in accordance with an embodiment.

In FIG. 9E, uncured silicone 958 is applied upon the bottom mold so as to coat the bottom and sides. It is then partially cured at 65° C. for 30 minutes. The partially cured silicone 958 can optionally be removed from the mold.

Figure 9F:
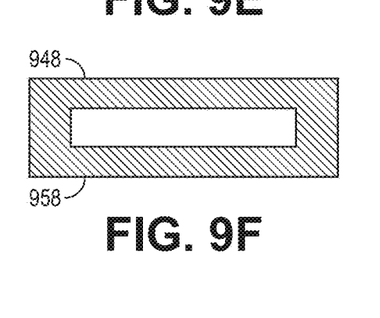
FIG. 9F illustrates a cured device in accordance with an embodiment.

In FIG. 9F, the top and bottom partially cured halves are aligned and joined together. The metal tube is between the halves. The assembly is fully cured at 100° C. for 8 hours.

The absorption bag and discharge sac are then masked, and the assembly is placed in a chemical vapor deposition (CVD) chamber for depositing parylene around the cannula. A thin layer of parylene C ensures that the cannula is non-permeable. Other areas of the device may be selectively coated with parylene, to various depths, to alter permeability.

Figure 10:
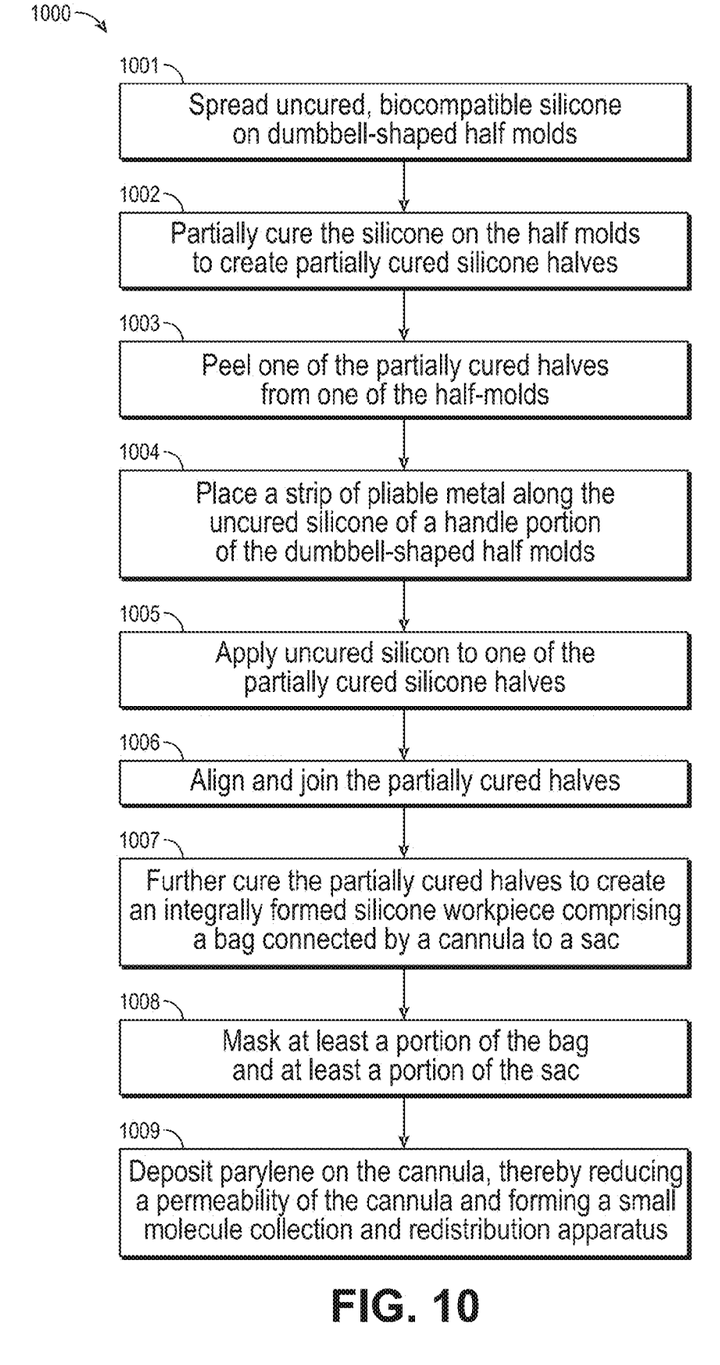
FIG. 10 is a flowchart illustrating a process in accordance with an embodiment.

FIG. 10 is a flowchart illustrating process 1000 in accordance with an embodiment. In operation 1001, uncured, biocompatible silicone is spread on dumbbell-shaped half molds. In operation 1002, the silicone on the half molds is partially cured to create partially cured silicone halves. In operation 1003, one of the partially cured halves is peeled from one of the half molds. In operation 1004, a strip of pliable metal is placed along the uncured silicone of a handle portion of the dumbbell-shaped half molds. In operation 1005, uncured silicone is applied to one of the partially cured silicone halves. In operation 1006, the partially cured halves are aligned and joined. In operation 1007, the partially cured halves are further cured in order to create an integrally formed silicone workpiece comprising a bag connected by a cannula to a sac. In operation 1008, at least a portion of the bag and at least a portion of the sac are masked. In operation 1009, parylene is deposited on the cannula, thereby reducing a permeability of the cannula and forming a small molecule collection and redistribution apparatus.

Figure 11:
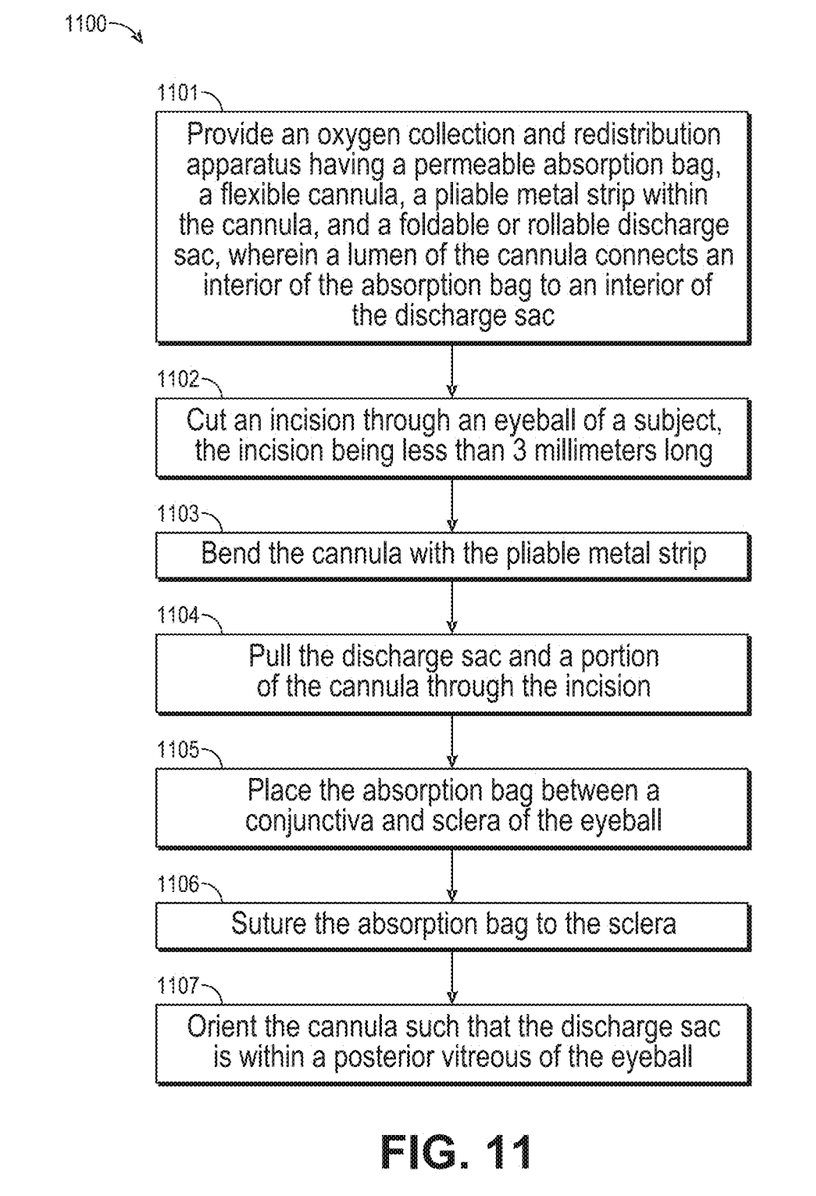
FIG. 11 is a flowchart illustrating a process in accordance with an embodiment.

FIG. 11 is a flowchart illustrating process 1100 in accordance with an embodiment. In operation 1101, an oxygen collection and redistribution apparatus having a permeable absorption bag, a flexible cannula, a pliable metal strip within the cannula, and a foldable or rollable discharge sac are provided. A lumen of the cannula connects an interior of the absorption bag to an interior of the discharge sac. In operation 1102, an incision is cut through an eyeball of a subject, the incision being less than 3 millimeters long. In operation 1103, the cannula with the pliable metal strip is bent into position. In operation 1104, the discharge sac and a portion of the cannula is pulled through the incision. In operation 1105, the absorption bag is placed between a conjunctiva and a sclera of the eyeball. In operation 1106, the absorption bag is sutured to the sclera. In operation 1107, the cannula is oriented such that the discharge sac is within a posterior vitreous of the eyeball.

The invention has been described with reference to various specific and illustrative embodiments. However, it should be understood that many variations and modifications may be made while remaining within the spirit and scope of the following claims.

What is claimed is:

1. A biocompatible, implantable apparatus for collecting and redistributing a predetermined class of small molecules within a body, the apparatus comprising:
   a permeable absorption bag, the bag being permeable to a predetermined class of small molecules, the bag defining an interior;
   a flexible cannula having a lumen, the cannula having a portion that is nonpermeable to the small molecules; and
   a foldable or rollable discharge sac, the sac being permeable to the small molecules, the sac defining an interior,
   wherein the lumen of the cannula connects the interior of the absorption bag to the interior of the discharge sac.

2. The apparatus of claim 1 further comprising:
   a pliable strip attached to the cannula and adapted to maintain the cannula in a bent or straight shape.

3. The apparatus of claim 2 wherein the pliable strip is enclosed within the cannula.

4. The apparatus of claim 2 wherein the pliable strip includes a foil, sheet, rod, or tube.

5. The apparatus of claim 2 wherein the pliable strip is comprised of a metal.

6. The apparatus of claim 1 wherein at least a portion of the absorption bag, cannula, and discharge sac are integrally formed of silicone.

7. The apparatus of claim 6 wherein the cannula further comprises:
   a coating of parylene over the silicone of the cannula, thereby reducing a permeability of the cannula.

8. The apparatus of claim 1 wherein absorption bag, cannula, and discharge sac are produced by micro-fabrication and thus have squared edges and are approximately a same height.

9. The apparatus of claim 1 further comprising:
a tab extending from the absorption bag, the flap having a suture hole therethrough.

10. The apparatus of claim 1 further comprising:
a handle extending from the absorption bag, the handle suitable for tugging with a surgical tool.

11. The apparatus of claim 1 wherein the discharge sac is toroidal shaped, an inner diameter of the toroidal shaped discharge sac being equal to or greater than 6 millimeters.

12. The apparatus of claim 1 further comprising:
at least one pillar within the cannula, the at least one pillar adapted to keep the cannula lumen from pinching closed.

13. The apparatus of claim 1 wherein the cannula has a perimeter less than or equal to 6 millimeters, thereby enabled to be fit through a 3 millimeter incision in a pars plana.

14. The apparatus of claim 1 wherein the predetermined class of small molecules includes diatomic oxygen ($O_2$).

15. The apparatus of claim 14 further comprising:
a perfluorocarbon within the absorption bag for oxygen solubility.

16. The apparatus of claim 14 further comprising:
a hemeprotein within the absorption bag for oxygen transport.

17. The apparatus of claim 16 wherein the hemeprotein includes natural, artificial, or autologous hemoglobin or myoglobin.

18. The apparatus of claim 14 further comprising:
a chlorocruorin or a hemocyanin within the absorption bag for oxygen transport.

19. The apparatus of claim 1 wherein the predetermined class of small molecules includes carbon dioxide ($CO_2$) or nitrous oxide ($N_2O$).

20. A method of manufacturing an implantable small molecule collection and redistribution apparatus, the method comprising:
spreading uncured, biocompatible silicone on dumbbell-shaped half molds;
partially curing the silicone on the half molds to create partially cured silicone halves;
peeling one of the partially cured halves from one of the half-molds;
applying uncured silicon to one of the partially cured silicone halves;
aligning and joining the partially cured halves;
further curing the partially cured halves to create an integrally formed silicone workpiece comprising a bag connected by a cannula to a sac;
masking at least a portion of the bag and at least a portion of the sac; and
depositing parylene on the cannula, thereby reducing a permeability of the cannula and forming a small molecule collection and redistribution apparatus.

* * * * *